United States Patent [19]
Tadokoro et al.

[11] 3,959,344
[45] May 25, 1976

[54] PROCESS FOR THE PREPARATION OF DIAMINOMALEONITRILE

[75] Inventors: Yukio Tadokoro, Tokyo; Tadao Shirai, Mobara; Satoshi Sogabe, Mobara; Seikichi Yoshikawa, Mobara, all of Japan

[73] Assignee: Nippon Chemicals Co., Ltd., Tokyo, Japan

[22] Filed: Dec. 17, 1974

[21] Appl. No.: 533,473

Related U.S. Application Data

[63] Continuation of Ser. No. 314,034, Dec. 11, 1972, abandoned.

[52] U.S. Cl. ......................................... 260/465.5 R
[51] Int. Cl.² ........................................ C07C 120/00
[58] Field of Search ............................. 260/465.5 R

[56] References Cited
UNITED STATES PATENTS

| | | | |
|---|---|---|---|
| 2,499,441 | 3/1950 | Woodward | 260/465.5 R |
| 2,722,540 | 11/1955 | Carter | 260/465.5 R |
| 2,818,423 | 12/1957 | Carter | 260/465.5 R |
| 3,551,473 | 12/1970 | Hartter | 260/465.5 R |
| 3,564,039 | 2/1971 | Webster | 260/465.5 R |
| 3,629,318 | 12/1971 | Webster | 260/465.5 R |
| 3,839,406 | 10/1974 | Hara et al. | 260/465.5 R |
| 3,840,582 | 10/1974 | Okada | 260/465.5 R |
| 3,842,115 | 10/1974 | Hamamoto et al. | 260/465.5 R |
| 3,862,205 | 1/1975 | Webster | 260/465.5 R |
| 3,894,071 | 7/1975 | Nishiwaki et al. | 260/465.5 R |
| 3,897,477 | 7/1975 | Hamamoto et al. | 260/465.5 R |

*Primary Examiner*—Joseph P. Brust
*Attorney, Agent, or Firm*—Armstrong, Nikaido & Wegner

[57] ABSTRACT

In the preparation of diaminomaleonitrile by polymerization of hydrogen cyanide, the improvement which comprises employing, as a reaction solvent, at least one mononitrile compound selected from the group consisting of saturated aliphatic mononitriles containing 2 to 4 carbon atoms, methacrylonitrile and aromatic mononitriles.

10 Claims, No Drawings

PROCESS FOR THE PREPARATION OF DIAMINOMALEONITRILE

This is a continuation, of application Ser. No. 314,034, filed Dec. 11, 1972, now abandond.

This invention relates to a process for the preparation of diaminomaleonitrile and, more particularly, to an improved process for the preparation of diaminomaleonitrile by polymerizing hydrogen cyanide in the presence of a basic substance employing a mononitrile as a solvent.

Diaminomaleonitrile is known as a tetramer of hydrogen cyanide, having the structural formula:

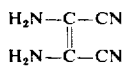

and is of great value as a starting compound for the synthesis of various heterocyclic compounds, especially as a raw material for the manufacture of intermediates and medicinal compounds, such as dicvanopyrazine, adenine and dicyanoimidazole, various stabilizers, agricultural chemicals and additives for foodstuffs. However, it has been of a very high price because there has not been developed any favorable process for the synthesis thereof.

In a prior process, diaminomaleonitrile has been prepared by polymerizing hydrogen cyanide in a solvent in the presence of a basic compound, such as alkali cyanides, trialkylamines or organic quaternary ammonium hydroxide, and extracting diaminomaleonitrile from the resulting polymerizate by means of a solvent. This prior process, however, is low in reaction rate and in yield. For instance, according to U.S. Pat. No. 2,722,540, 35 g of hydrogen cyanide was polymerized in methanol in the presence of 0.14 g of benzyltrimethylammonium hydroxide as a catalyst for a time as long as 140 hours to obtain only 9.8 g of a polymerizate (28% by weight of theoretical yield based on the weight of hydrogen cyanide charged) containing therein diaminomaleonitrile in a content of only 19.5 to 25.6%.

In Published Specification of Unexamined Japanese Patent application, Publication No. 2917/1971, there has been disclosed a process for the preparation of diaminomaleonitrile in high yields by employing cyanogen. In this process diaminomaleonitrile is prepared at high reaction rates and in high yields by employing cyanogen. However, this process disadvantageously needs apparatus and work for previously preparing cyanogen in very high yields which will make the product expensive and the procedure complicated.

Other than these processes, a process for polymerizing hydrogen cyanide by employing an alkali cyanide as a catalyst and dimethylsulfoxide as a solvent has been disclosed in Offenlegungsschrift 2,022,243 (West Germany). This process is excellent in yield, but it encounters a difficulty in recovery of the solvent from reaction mixture and needs a complicated post-treatment procedure for isolation of the end product diaminomaleonitrile. Namely, dimethylsulfoxide used as the solvent is apt to react with the polymerizate of hydrogen cyanide and, while the reaction product is dissolved in hot water and the end product is isolated from the resulting solution by liquid-liquid extraction by means of ether leaving an aqueous dimethylsulfoxide solution containing unextracted polymerizates, it is very difficult to separate dimethylsulfoxide from water without recovery loss, and, thus, the post treatment of the reaction mixture is complicated.

Accordingly, an object of the present invention is to provide an improved process for the preparation of diaminomaleonitrile.

Another object of the present invention is to provide a process for the preparation of diaminomaleonitrile in high yields from hydrogen cyanide.

A still another object of the present invention is to provide a process for producing diaminomaleonitrile at very low costs in very simplified procedure.

A further object of the present invention is to provide a novel solvent for the preparation of diaminomaleonitrile by polymerization of hydrogen cyanide.

The aforesaid objects of the present invention are accomplished by employing as a reaction solvent at least one mononitrile selected from the group consisting of saturated aliphatic mononitriles containing 2 to 4 carbon atoms in molecule, methacrylonitrile, aromatic mononitriles in the preparation of diaminomaleonitrile by polymerization of hydrogen cyanide.

In accordance with the process of the present invention, diaminomaleonitrile is prepared by polymerizing hydrogen cyanide in a mononitrile compound selected from the group consisting of saturated aliphatic mononitriles containing 2 to 4 carbon atoms in molecule, methacrylonitrile, aromatic mononitriles and mixtures thereof, in the presence of a basic compound.

The mononitrile employed in the practice of the process of the present invention includes; acetonitrile, propionitrile, n-butylonitrile, isobutylonitrile and like saturated aliphatic mononitriles containing 2 to 4 carbon atoms in molecule; methacrylonitrile; and benzonitrile, o-tolunitrile, m-tolunitrile, p-tolunitrile and like aromatic mononitriles. The solvent is used in amounts in the weight ratios to hydrogen cyanide usually of 1 to 100:1 preferably of from 2 to 20.

Separation of polymerizates of hydrogen cyanide from a mixture with a saturated aliphatic mononitrile or methacrylonitrile is achieved conveniently by subjecting the mixture to distillation under reduced pressure. On the other hand, separation of diaminomaleonitrile from a mixture with an aromatic mononitrile is attained by stirring the mixture with water added thereto to extract the diaminomaleonitrile into aqueous phase. The separation may also be attained by adding to the mixture five times its volume or more quantities of benzene, toluene, xylene or like hydrocarbon solvent to precipitate solid polymerizates and separating the solid precipitate by filteration.

The basic compound suitably used as catalyst includes: e.g., trimethylamine, triethylamine, tri-n-propylamine, tri-isopropylamine, tri-n-butylamine, tri-isobutylamine, tripentylamines, trihexylamines, triheptylamines, trioctylamines and like tertiary amines; tetramethylammonium hydroxide, benzyl trimethylammonium hydroxide, phenyl trimethylammonium hydroxide, phenyl triethylammonium hydroxide, dimethyl ethyl beta-chloroethylammonium hydroxide and like quaternary ammonium hydroxide; and sodium cyanide, potassium cyanide, lithium cyanide and like alkali metal cyanides. Among these basic compounds, tertiary amines are most suitable as catalyst since they have high solubilities in such solvents as mentioned above and can be used in variable molar ratio to hydrogen cyanide.

The tertiary amine and quaternary ammonium hydroxide may be used in amounts of the molar ratio to hydrogen cyanide of from 0.02 to 5, preferably from 0.05 to 2 and more desirably from 0.1 to 1. The molar ratio less than 0.02 results in a low yield, while that exceeding 5 leads to excessive decrease in concentration of solvent and of hydrogen cyanide rather to lower the rate of reaction. Although the alkali metal cyanide remains undissolved when used in large quantities because of its low solubility in the solvent, it may be used in an amount over its solubility without any adverse effect.

The reaction in accordance with the present invention is usually conducted at a temperature within the range from 10° to 140°C, preferably from 30° to 140°C and more desirably from 40° to 120°C. At a temperature below 10°C, the reaction rate is too low and, in addition, the conversion of hydrogen cyanide and the selectivity to diaminomaleonitrile are insufficient. On the other hand, at reaction temperatures exceeding 140°C, yields of higher polymerizates increase remarkably to suddenly reduce the selectivity to diaminomaleonitrile. Carrying out the reaction at a temperature within the aforesaid temperature range, reaction times are shortened and, in addition, it is possible to obtain diaminomaleonitrile at high selectivity because of high conversion of hydrogen cyanide to polymerizate and diminution of side reactions. The polymerizate obtained is high in purity of diaminomaleonitrile.

The reaction pressure varies depending on the solvent used and the reaction temperature employed. For instance, when acetonitrile is used as a solvent, the reaction may be carried out under normal pressure to a reaction temperature of about 70°C.

The reaction time varies depending on the reaction temperature within the range of usually from 1 hour to 7 days, preferably from 2 hours to 60 hours and more desirably from 3 hours to 48 hours. Reaction time less than 1 hour is insufficient to obtain a high yield, while reaction time over 7 days do not bring about higher yields but bring about increase of side reactions.

The reaction may be conducted batch-wise or continuously.

As mentioned above, in accordance with the process of the present invention, a high conversion of hydrogen cyanide to polymer and a high selectivity to diaminomaleonitrile are obtained by employing a mononitrile selected from the group consisting of saturated aliphatic mononitriles containing 2 to 4 carbon atoms in molecule, methacrylonitrile and aromatic mononitriles, as a reaction solvent and, consequently, the end product, diaminomaleonitrile is obtainable in a high purity and a high yield. The process of the present invention is operable in a simple way because of ease of separation of the aforesaid mononitrile from reaction mixture. Thus, in accordance with the process of the present invention, it is possible to produce diaminomaleonitrile in a simple procedure at a very low cost.

The process of the present invention will be illustrated in more detail by the following examples in which the term "conversion to polymer" means the percentage by weight of hydrogen cyanide polymer formed to hydrogen cyanide charged and the term "selectivity" means the percentage by weight of diaminomaleonitrile in the polymer formed.

EXAMPLE 1

In a round-bottomed flask of a capacity of 300 ml there was charged 135 g of propionitrile, then added thereto 27 g of hydrogen cyanide and 10 g of triethylamine. The flask was then put in a thermostat and maintained at 20°C. After 44 hours, the flask was taken out of the thermostat and the reaction mixture was subjected to distillation under reduced pressure to distill off unreacted hydrogen cyanide, triethylamine and propionitrile at temperature range of 40° to 45°C. Thus, there was obtained 6.78 g of a polymerizate (conversion to polymer, 25.1 %). The polymerizate was extracted at 40°C using 140 ml of isobutanol. The extract was heated at 40° to 45°C under reduced pressure to evaporate isobutanol. Thus, there was obtained 4.47 g of a solid extract. The extract was subjected to thin layer chromatography to separate a spot of diaminomaleonitrile and to assay by ultraviolet spectrophotometer using an wave length of 295 m$\nu$. The assay indicated a content of 63.2 % of diaminomaleonitrile in the solid extract. Accordingly, the selectivity to diaminomaleonitrile is 41.6 % in polymerizate of hydrogen cyanide.

EXAMPLE 2

In the same apparatus as in Example 1, there were added 20 g of hydrogen cyanide and 7.5 g of triethylamine to 135 g of acetonitrile. After maintained at 40°C for 44 hours, the reaction mixture was filtered to recover 2.16 g of an insoluble polymer which contained no diaminomaleonitrile. The filtrate was distilled under reduced pressure to distill off unreacted hydrogen cyanide, triethylamine and acetonitrile at 40° to 45°C. Thus, there was obtained 5.77 g of a polymer. Assay of the polymer in the same manner as in Example 1 indicated the purity of diaminomaleonitrile to be 56.3 %. Accordingly, the total weight of hydrogen cyanide polymerizates obtained was 7.93 g (conversion to polymer 39.7 %), 3.25 g (selectivity 41.0 159 %) of which was diaminomaleonitrile.

EXAMPLE 3

In the same apparatus as in Example 1, there were added 27 g of hydrogen cyanide and 10 g of tributylamine to 135 g of n-butylonitrile. After maintained at 35°C for 44 hours, the liquid reaction mixture was distilled under reduced pressure to distill off unreacted hydrogen cyanide, portion of tributylamine and n-butylonitrile at 40° to 45°C. Tributylamine contained in the residue was eliminated by washing the residue 3 times repeatedly by 100 ml, in total, of xylene. Thus, there was obtained 8.23 g of a polymer (conversion to polymer 30.5 %). The polymer was extracted at 40°C by means of 140 ml of isobutanol to obtain a solid extract of 5.69 g. Assay in the same manner as in Example 1 of the solid extract indicated a content of diaminomaleonitrile of 61.7 %. Accordingly, the yield of dimethylmaleonitrile was 3.51 g and the selectivity to diaminomaleonitrile against the whole polymer was 42.5 %.

EXAMPLE 4

In the same apparatus as in Example 1 there were charged 135 g of acetonitrile, 27 g of hydrogen cyanide and 2.5 g of sodium cyanide. The content of the flask was maintained at 20°C for 73 hours with intermittently shaking. The reaction mixture was then withdrawn from the flask and distilled under reduced pressure to eliminate unreacted hydrogen cyanide and acetonitrile at 40° to 45°C. The mixture of a hydrogen cyanide polymer and sodium cyanide remained was dried under reduced pressure and weighed. Deducting the weight of sodium cyanide from the weight of the dried mixture, the weight of the hydrogen cyanide polymer was 2.04 g (conversion to polymer 7.55 %). The polymer was extracted by means of isobutanol to obtain 1.53 g of a solid extract. Assay of the extract indicated a purity of 74.3 %. Accordingly, a selectivity to diaminomaleonitrile in the hydrogen cyanide polymer is 55.7 %.

EXAMPLE 5

In the same apparatus as in Example 1 there were charged 135 g of acetonitrile, 18.2 g of hydrogen cyanide and 34 g of triethylamine, and the mixture was maintained at 35°C for 10 hours. The mixture was then treated in the similar manner as in Example 1 to obtain 2.66 g (conversion to polymer 14.6 %) of a hydrogen cyanide polymer. The polymer was extracted by isobutanol to obtain a solid extract of 1.87 g. Assay of the extract indicated a diaminomaleonitrile content of 72.3 %. Accordingly, the selectivity to diaminomaleonitrile in the whole hydrogen cyanide polymer is 50.9 %.

EXAMPLE 6

In a 300 ml three-necked flask equipped with a reflux condenser and a thermometer there were charged 135 g of acetonitrile, 18.2 g (0.675 mol) of hydrogen cyanide and 13.6 g (0.135 mol) of triethylamine. The flask was externally heated to maintain the content at 60°C while circulating ice-cooled water through the reflux condenser. On this occasion, there was observed reflux of a small amount of liquid in the reflux condenser. After 10 hours, the reaction mixture was cooled, transferred into a rotary evaporator and distilled under reduced pressure to recover unreacted hydrogen cyanide, acetonitrile and triethylamine. The weight of a polymer remained in the evaporator was 6.83 g, corresponding to a conversion to polymer of 37.5 %.

The polymer was extracted by isobutanol at temperatures below 50°C to obtain 4.27 g of a solid extract, crude diaminomaleonitrile. The purity of the crude diaminomaleonitrile was determined to be 75.6 % by fractionating a spot of diaminomaleonitrile by means of thin layer chromatography and assaying the fraction by means of an ultraviolet spectrophotometer using a wave length of 295 m$\nu$. Therefore, the selectivity to diaminomaleonitrile against the whole hydrogen cyanide polymer was 47.2 %.

EXAMPLE 7

In the same apparatus as in Example 6 there were charged 135 g of acetonitrile, 18.2 g (0.675 mol) of hydrogen cyanide and 34.4 g (0.34 mol) of triethylamine. The flask was externally heated to maintain an inner temperature of 60°C for 3 hours thereby to effect polymerization. The reaction mixture was then distilled under reduced pressure in a rotary evaporator as in Example 6 to recover unreacted hydrogen cyanide, acetonitrile and triethylamine. The weight of a hydrogen cyanide polymer remained in the evaporator was 2.46 g (conversion to polymer 13.6 %). The polymer was extracted by isobutanol to obtain 2.32 g of a solid extract. The extract was determined to be of a purity of 82.2 %. Accordingly, the selectivity to diaminomaleonitrile determined based on the weight of whole polymer was 77.7 %.

EXAMPLE 8

In a 300 ml autoclave there were charged 100 g of propionitrile, 13.5 g (0.5 mol) of hydrogen cyanide and 25.3 g (0.251 mol) of triethylamine, and the charge was maintained at 80°C for 3 hours. The reaction mixture was then cooled to temperatures below 20°C, taken out of the autoclave and distilled under reduced pressure to recover unreacted hydrogen cyanide, propionitrile and triethylamine and to obtain 3.11 g of a polymer (conversion to polymer 23.1 %). The polymer was extracted by isobutanol to obtain a solid extract of 2.01 g of a purity of 78.1 % with respect to diaminomaleonitrile as determined by purity assay in a similar manner. Therefore, the selectivity to diaminomaleonitrile amounted to 50.5 % of the whole polymer.

EXAMPLE 9

In the same autoclave as in Example 8 there were charged 100 g of acetonitrile, 13.5 g (0.5 mol) of hydrogen cyanide and 25.3 g (0.25 mol) of triethylamine, and the charge was maintained at 120°C for 3 hours. In the course of reaction, the maximum pressure indicated was 3.1 Kg/cm$^2$ G. The reaction mixture was then treated in the same manner as in Example 8 to obtain 8.01 g of a polymer (conversion to polymer 59.4 %). The polymer was extracted by isobutanol to obtain 4.64 g of a solid extract of a purity of 72.3 % with respect to diaminomaleonitrile as determined by purity assay in a similar manner. Therefore, the selectivity to diaminomaleonitrile was 41.8 %.

EXAMPLE 10

In the same apparatus as in Example 6 there were charged 135 g of p-tolunitrile, 18.2 g (0.675 mol) of hydrogen cyanide and 13.6 g (0.135 mol) of triethylamine, and the flask was externally heated to maintain its inner temperature at 60°C for 6 hours. The reaction mixture was then distilled in a rotary evaporator to recover the whole of unreacted hydrogen cyanide and of triethylamine and about one half of p-tolunitrile. Distillation of p-tolunitrile was carried out under a reduced pressure below 5 mm Hg while externally heating at temperatures not exceeding 100°C.

The concentrate thus obtained was poured into 500 ml of xylene to precipitate a solid polymer of hydrogen cyanide. The precipitate was filtered, washed with 100 ml of xylene and dried to obtain 9.67 g of a polymer (conversion to polymer 53.2 %). The polymer was extracted by isobutanol to obtain 7.62 g of a solid extract of a purity of 76.3 % with respect to diaminomaleonitrile. Therefore, the selectivity to diaminomaleonitrile was calculated to be 60.3 %.

EXAMPLE 11

In a similar autoclave as in Example 8 there were charged 50 g of acetonitrile, 6.75 g (0.25 mol) of hydrogen cyanide and 50.5 g (0.5 mol) of triethylamine, and the charge was heated at 180°C for 3 hours to effect polymerization. The maximum reaction pressure indicated was 1.8 Kg/cm$^2$ G. The reaction mixture was then treated in a similar manner as in Example 8 to obtain 3.36 g of a polymer of hydrogen cyanide (conversion to polymer 49.8 %). The polymer was extracted by isobutanol to obtain 1.82 g of a solid extract of a purity of 70.3 % with respect to diaminomaleonitrile. Accordingly, the selectivity to diaminomaleonitrile was 38.2 % in the whole polymer.

EXAMPLES 12 to 16

Polymerization of hydrogen cyanide was carried out using a similar autoclave as in Example 8, 100 g of a nitrile, as listed in the following Table 1, 13.5 g of hydrogen cyanide and 0.5 mol, per mol of hydrogen cyanide, of a trialkylamine, as listed in the Table 1, to obtain the results as summarized in the Table 1.

Table 1

| Ex. No. | Solvent | Amine | Reaction temp. (°C) | Reaction time(hrs) |
|---|---|---|---|---|
| 12 | Isobutylonitrile | Triethylamine | 80 | 3 |
| 13 | Methacrylonitrile | Tributylamine | 60 | 5 |
| 14 | Benzonitrile | Triethylamine | 50 | 3 |
| 15 | m-Tolunitrile | Trimethylamine | 60 | 5 |
| 16 | o-Tolunitrile | Triethylamine | 50 | 5 |

| Conversion to polymer (%) | Selectivity (%) |
|---|---|
| 24.1 | 54.6 |
| 28.2 | 46.1 |
| 41.3 | 33.0 |
| 58.2 | 43.1 |
| 26.3 | 35.7 |

EXAMPLE 17

In a 300 ml round-bottomed flask with an air-tight stopper there were charged 135 g of methacrylonitrile, 27 g (1 mole) of hydrogen cyanide and 20.2 g (0.2 mol) of triethylamine. The flask was then put in a thermostat to maintain at 35°C for 24 hours. Thereafter, the reaction mixture was taken out of the flask and distilled under reduced pressure to distill off unreacted hydrogen cyanide, triethylamine and methacrylonitrile at 40° to 45°C and to recover 9.07 g (conversion to polymer 33.6 %) of a hydrogen cyanide polymer. The polymer was extracted at 40°C by means of 140 ml of isobutanol to obtain 6.57 g of a solid extract. The solid extract was a crude diaminomaleonitrile of a purity of 70.8 %. Therefore, the selectivity to diaminomaleonitrile of the polymerized hydrogen cyanide was calculated as 51.2 %.

EXAMPLE 18

In the same apparatus as in Example 17 there were charged 135 g of isobutylonitrile, 20 g (0.74 mol) of hydrogen cyanide and 37.4 g (0.37 mol) of triethylamine. After maintained at 35°C for 24 hours, the reaction mixture was distilled under reduced pressure to distill off unreacted hydrogen cyanide, triethylamine and isobutylonitrile at 40° to 45°C and to recover 6.40 g of a hydrogen cyanide polymer (conversion to polymer 32.0 %). The polymer was extracted at 40°C by means of 140 ml of isobutanol to obtain 4.91 g of a solid extract of a purity of 71.6 % with respect to diaminomaleonitrile as determined by ultraviolet spectrophotometrical assay as in Example 1. Therefore, the selectivity to diaminomaleonitrile of the polymerized hydrogen cyanide was calculated as 54.9 %.

EXAMPLE 19

In the same apparatus as in Example 17 there were charged 135 g of bennonitrile, 18.2 g (0.675 mol) of hydrogen cyanide and 34.1 g (0.358 mol) of triethylamine. After maintained at 35°C for 5 hours, the reaction mixture was transferred into a rotary evaporator and concentrated under reduced pressure at temperatures not exceeding 100°C on a water bath until the content was concentrated to about one third times its original volume or less. The concentrate was then poured into 500 ml of xylene to precipitate a hydrogen cyanide polymer. The precipitate was filtered, washed with 50 ml of xylene and dried to obtain 5.8 g of a polymer (conversion to polymer 31.8 %). The polymer was extracted by isobutanol to obtain 3.62 g of a solid extract of a purity of 66.7 % with respect to diaminomaleonitrile as indicated by ultraviolet spectrooptometrical assay. Therefore, the selectivity to diaminomaleonitrile was 41.6 %.

EXAMPLE 20

In the same apparatus as in Example 17 there were charged 135 g of o-tolunitrile, 18.2 g of hydrogen cyanide (0.675 mol) and 34 g (0.34 mol) of triethylamine. After maintained at 35°C for 5 hours, the reaction mixture was transferred into a rotary evaporator and concentrated under reduced pressure at temperatures not exceeding 100°C on a water bath until the content was concentrated to one third times its original volume while recovering distilled unreacted hydrogen cyanide and o-tolunitrile by liquefaction. The concentrate was then poured into 500 ml of xylene to precipitate a hydrogen cyanide polymer. The precipitate was recovered by filteration, washed with 50 ml of xylene and dried to obtain 2.59 g of a dried polymer (conversion to polymer 14.2 %). The polymer was extracted by isobutanol to obtain 1.48 g of a solid extract of a purity of 64.3 % with respect to diaminomaleonitrile. Therefore, the selectivity to diaminomaleonitrile of the polymerized hydrogen cyanide was calculated as 36.8 %.

EXAMPLE 21

In the same apparatus as in Example 17 there were charged 135 g of p-tolunitrile as solvent, 18.2 g of hydrogen cyanide (0.675 mol) and 58.2 g of tributylamine (0.34 mol). After allowed to stand still at 30°C for 5 hours, the reaction mixture was processed in a similar manner as in Example 20 to obtain 3.66 g of a hydrogen cyanide polymer (conversion to polymer 20.0 %). The polymer was extracted by isobutanol to obtain 2.48 g of a solid extract of a purity of 72.4 % with respect to diaminomaleonitrile. Thus, the selectivity to diaminomaleonitrile of the polymerized hydrogen cyanide was calculated as 49.1 %.

EXAMPLE 22

The same procedure as in Example 21 was repeated except for use of m-tolunitrile in place of p-tolunitrile to obtain 3.27 g of a hydrogen cyanide polymer (conversion to polymer 18.0 %) and 2.09 g of a solid isobutanol extract of a purity of 72.3 % with respect to diaminomaleonitrile. Thus, the selectivity to diaminomaleonitrile of the polymer was calculated as 46.2 %.

EXAMPLE 23

Acetonitrile and benzene were added to 25 g of 10 % aqueous tetraethyl ammonium hydroxide solution. A component containing 68.5 % by weight of benzene, 23.3 % by weight of acetonitrile and 8 % by weight of water was distilled off by azeotropic distillation. Then a bottom residue was subjected to gas chromatography. After recognizing no water content in the residue, it was used as a catalyst.

In the same apparatus as Example 6, there were charged 34 g (0.83 mol) of acetonitrile, 4.6 g (0.17 mol) of hydrogen cyanide and 2.5 g (0.017 mol) of above mentioned tetraethyl ammonium hydroxide. Polymerization was carried out by heating externally to maintain the content at 60°C for 4 hours. Then, it was transferred into a rotary evaporator to recover unreacted hydrogen cyanide and acetonitrile. A polymer of hydrogen cyanide was 1.27 g (conversion to polymer 27.6 %). The polymer was extracted to obtain 0.8 g of an extract. The extract contained 70 % of crude diaminomaleonitrile. Therefore, the selectivity to diaminomaleonitrile against the whole hydrogen cyanide polymer was 44.1 %.

What is claimed is:

1. A process for the preparation of diaminomaleonitrile comprising polymerizing at a temperature of from 30° to 140°C hydrogen cyanide in a solvent consists of a mononitrile selected from the group consisting of acetonitrile, propionitrile, n-butyronitrile, isobutyronitrile, methacrylonitrile, benzonitrile, o-tolunitrile, m-tolunitrile and p-tolunitrile in the presence of a basic compound, wherein the weight ratio of the mononitrile to hydrogen cyanide is 1:1 to 100:1.

2. A process of claim 1, wherein said mononitrile is methacrylonitrile.

3. A process of claim 1, wherein said mononitrile is benzonitrile, o-tolunitrile, m-tolunitrile or p-tolunitrile.

4. A process of claim 1, wherein said mononitrile is acetonitrile.

5. A process of claim 1, wherein said basic compound is selected from a tertiary amine or quaternary ammonium hydroxide thereof and an alkali metal cyanide.

6. A process of claim 5, wherein said basic compound is a tertiary amine.

7. A process of claim 6, wherein said tertiary amine is employed in a molar ratio to hydrogen cyanide of from 0.02 to 5.

8. A process of claim 5, wherein said basic compound is a quaternary ammonium hydroxide.

9. A process according to claim 8, wherein the molar ratio of said quaternary ammonium hydroxide hydrogen cyanide is from 0.02 to 5.

10. A process of claim 5, wherein said basic compound is an alkali metal cyanide.

* * * * *